US011207676B2

(12) United States Patent
Saunders

(10) Patent No.: US 11,207,676 B2
(45) Date of Patent: Dec. 28, 2021

(54) LAB-ON-A-CHIP (LOC) FOR BIOMIMETIC BONE REMODELING ANALYSIS

(71) Applicant: Marnie M. Saunders, Canton, OH (US)

(72) Inventor: Marnie M. Saunders, Canton, OH (US)

(73) Assignee: The University of Akron, Akron, OH (US)

( * ) Notice: Subject to any disclaimer, the term of this patent is extended or adjusted under 35 U.S.C. 154(b) by 222 days.

(21) Appl. No.: 15/963,360

(22) Filed: Apr. 26, 2018

(65) Prior Publication Data

US 2019/0126269 A1    May 2, 2019

Related U.S. Application Data

(60) Provisional application No. 62/527,241, filed on Jun. 30, 2017.

(51) Int. Cl.
*B01L 3/00* (2006.01)
*C12N 5/077* (2010.01)
(Continued)

(52) U.S. Cl.
CPC ....... *B01L 3/5027* (2013.01); *B01L 3/502761* (2013.01); *C12M 23/12* (2013.01); *C12N 5/0068* (2013.01); *C12N 5/0643* (2013.01); *C12N 5/0654* (2013.01); *G01N 15/00* (2013.01); *B01L 2300/042* (2013.01); *B01L 2300/0829* (2013.01); *B01L 2300/16* (2013.01);
(Continued)

(58) Field of Classification Search
None
See application file for complete search history.

(56) References Cited

U.S. PATENT DOCUMENTS

2019/0015423 A1* 1/2019 Jacobs ................ A61K 31/473

OTHER PUBLICATIONS

Teti et al., Osteoblast-Osteoclast relationships in bone resorption: osteoblasts enhance osteoclast activity in a serum-free co-culture system, 1991, Biochemical and Biophysical Research Communications, vol. 179 No. 1, pp. 634-640 (Year: 1991).*

(Continued)

*Primary Examiner* — Holly Kipouros
(74) *Attorney, Agent, or Firm* — Renner, Kenner, Greive, Bobak, Taylor & Weber

(57) ABSTRACT

A lab-on-a-chip (LOC) for the biomimetic study of the multicellular interactions of bone cells includes a PDMS substrate and cap, which together form one or more wells that are fluidly coupled by tubes. The wells are configured to support various bone cells and related cellular support substrates therein, while the tubes allow conditioned medium (CM), including soluble signals, and various other co-factors to be communicated among the various wells. By controlling the configuration among and between various bone cells in the wells, the temporal and spatial limitations associated with traditional in vivo bone tissue models is removed. In addition, the LOC enables a particular research objective to be studied by allowing the user to configure the arrangement of the wells/tubes of the LOC, so as to control the manner in which bone cell soluble signals, bone cell contact, and bone cell matrix interaction interplay.

18 Claims, 11 Drawing Sheets

(51) Int. Cl.
  *C12M 1/32* (2006.01)
  *C12N 5/00* (2006.01)
  *C12M 3/00* (2006.01)
  *C12N 5/078* (2010.01)
  *G01N 15/00* (2006.01)
  *C12M 3/06* (2006.01)

(52) U.S. Cl.
  CPC ........ *B01L 2300/163* (2013.01); *C12M 21/08* (2013.01); *C12M 23/16* (2013.01); *C12N 2533/30* (2013.01); *C12N 2533/54* (2013.01)

(56) References Cited

OTHER PUBLICATIONS

Wei et al., Elucidating in vitro cell-cell interaction using a microfluidic coculture system, 2006, Biomed Microdevies, 8, pp. 65-71 (Year: 2006).*

Mitra et al., Scaffolds for bone tissue engineering: role of surface patterning on osteoblast response, 2013, RSC Advances, 3, pp. 11073-11094. (Year: 2013).*

Kang et al., IL-23 promotes osteoclastogenesis in osteoblast-osteoclast co-culture system, 2014, Genetics and Molecular Research , 13(2), pp. 4673-4679. (Year: 2014).*

Chen et al., Self-assembled composite matrix in a hierarchical 3-D scaffold for bone tissue engineering, 2011, Acta Biomaterialia, vol. 7, pp. 2244-2255 (Year: 2011).*

* cited by examiner

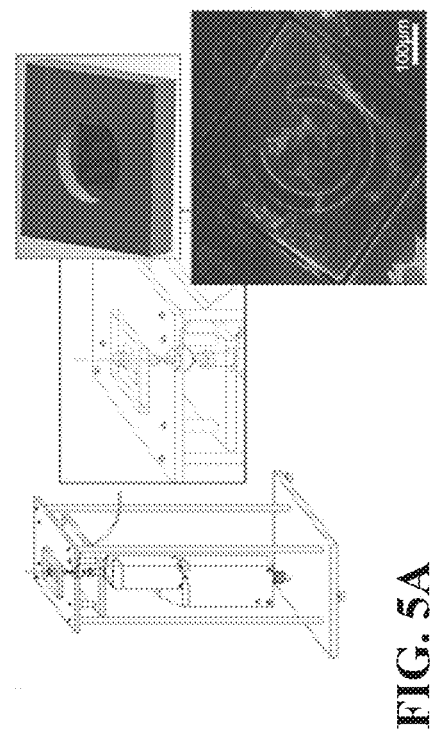
FIG. 5A
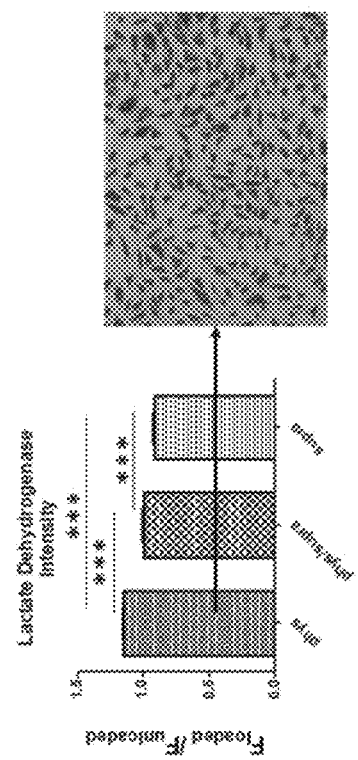
FIG. 5B
| FACTOR | PHYS | PHYS/SUPRA |
|---|---|---|
| NCAM-1 | 25% | 8% |
| NIDOGEN-1 | 3% | 7% |
| ANG-2 | 10% | 4% |
| GAL-3 | 4% | 3% |
| SFRP-3 | 70% | 15% |
| DECORIN | 25% | 25% |
| GASP-1 | 10% | 18% |
| TSP-1 | 28% | 25% |
| ARTEMIN | 1% | 53% |
| CALBINDIN-D | 5% | 5% |
| CNTF | 38% | 4% |
| PD-ECGF | 2% | 45% |
| PDGFRA | 6% | 35% |
| LACTOFERRIN | 14% | 74% |
| SAA | 14% | 45% |
| SERPIN F1 | 3% | 65% |
| VITRONECTIN | 9% | 72% |
| MIF | 21% | 5% |
| ANG-1 | 4% | 3% |
| ACTIVIN A | 27% | 85% |
| IL1R3 | 45% | 65% |
| TSP-2 | 4% | 68% |
| PERSEPHIN | 10% | 57% |
| EMMPRIN | 30% | 55% |
FIG. 5C FIG. 8A
FIG. 8B
FIG. 8D
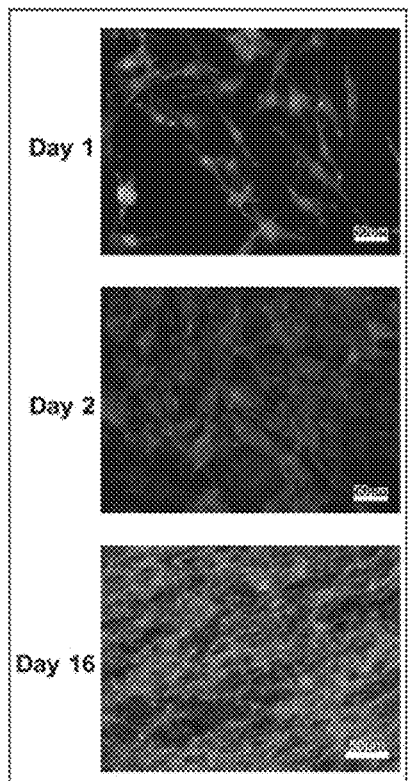
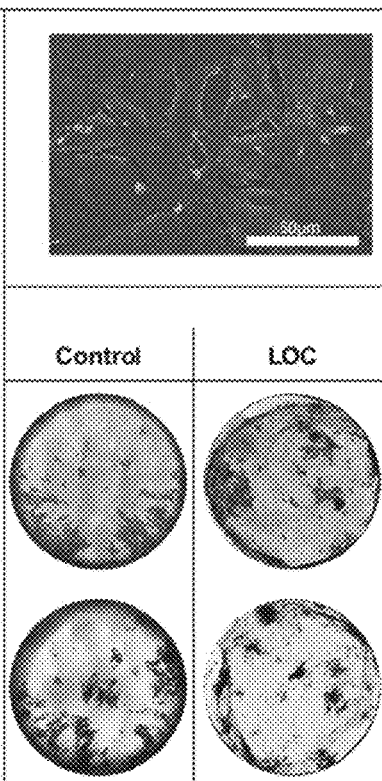
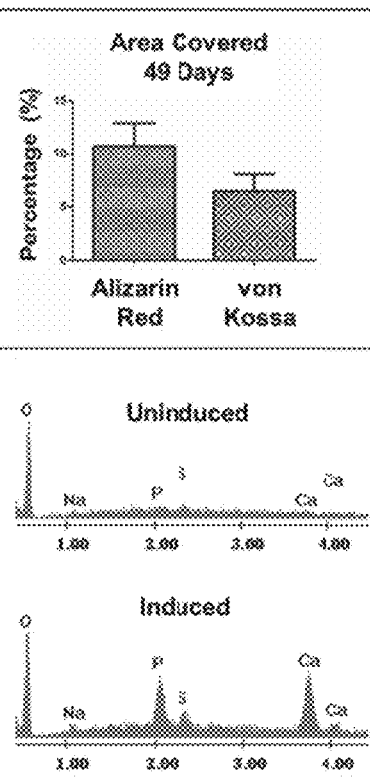
FIG. 8C
FIG. 8E

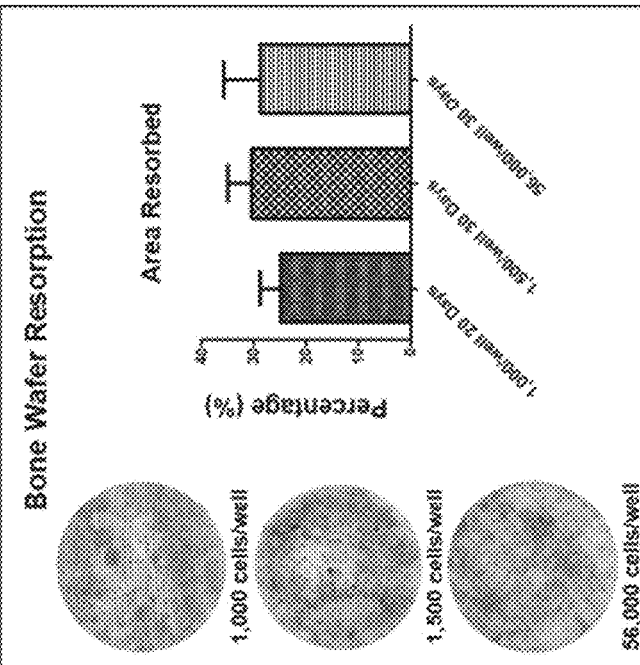
FIG. 9D    FIG. 9C
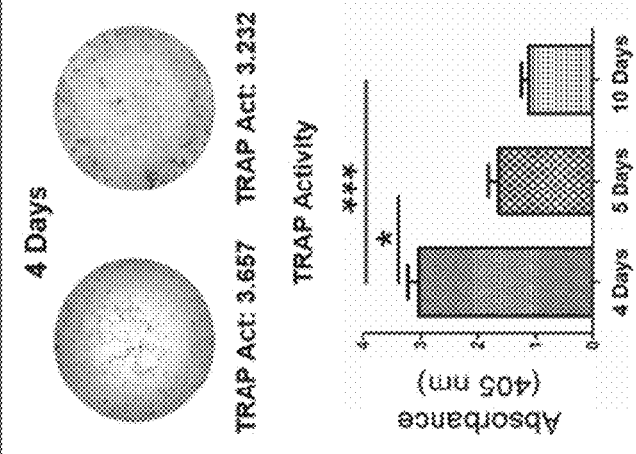
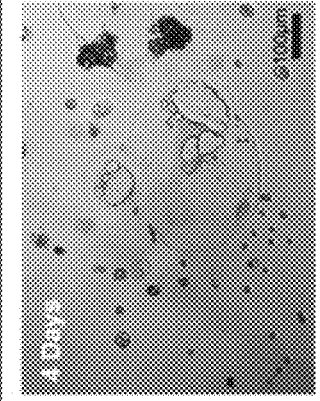
FIG. 9A    FIG. 9B

LAB-ON-A-CHIP (LOC) FOR BIOMIMETIC BONE REMODELING ANALYSIS

CROSS-REFERENCE TO RELATED APPLICATION

This application claims the benefit of U.S. Provisional Application No. 62/527,241 filed Jun. 30, 2017, the contents of which are incorporated herein by reference.

STATEMENT REGARDING FEDERALLY SPONSORED RESEARCH OR DEVELOPMENT

This invention was made with government support under contract no. 1060990 awarded by the National Science Foundation (NSF)—Division of Chemical Bioengineering, Environmental, and Transport Systems (CBET), and contract no. DE 022664 awarded by the National Institutes of Health (NIH)/National Institute of Dental and Craniofacial Research (NIDCR). The government has certain rights in the invention.

TECHNICAL FIELD

In general, the various embodiments disclosed herein relate to lab-on-a-chip (LOC) systems. In particular, the various embodiments disclosed herein are directed to LOCs configured for use in the research of bone cells. More particularly, the various embodiments disclosed herein are directed to biomimetic LOCs that support the multicellular interaction of bone cells, and their treatment with other co-factors to enable the quantification of functional outcomes of bone cell remodeling, including bone resorption and bone formation.

BACKGROUND

Lab-on-a-chip (LOC) systems house individual controlled environments that are unable to be replicated through other means. For example, LOCs have the ability to incorporate multifunctional elements to construct complete analytic microsystems, and have been proven applicable to research in the biological sciences, including genomics, proteomics, clinical diagnostics and drug discovery. Accordingly, LOCs have proven to be advantageous in cell culture. Researchers have used LOCs to isolate various cellular factors for study, as well as to simulate laboratory analysis and to model cellular, tissue and organ level processes. While such LOC technology has developed in various areas of biological science, the field of bone tissue remodeling has been slow to advance, and has failed to adopt the advantages that LOC systems can provide.

Presently, much of what is known about the response of bone cells to mechanical stimulation has been gathered from in vitro mechanotransduction studies in which cells are isolated as a single cell type in an artificial environment, in the absence of their native milieu. Unfortunately, such artificial systems are not able to adequately mimic the natural, in vivo physiologic environment of bone tissue, as well as fail to integrate many of the fundamental elements known to be crucial in mechnotransduction.

In addition, the use of traditional bone cell research techniques are complicated by the various behavioral characteristics of bone cells. For example, bone cells possess greatly dissimilar lifespans, in fact, the lives of osteocytes and osteoclasts differ by years, whereas the bone cell resorption phase of osteoclasts is about three weeks, and the formation phase of osteoblasts is about three months. Further, osteoblasts and osteoclasts are not observed in the same location simultaneously during the process of bone remodeling. Therefore, it would be desirable to have an LOC that is configured to remove the temporal and spatial restrictions of current bone cell research techniques, so as to enable the concurrent study of any combination of cell types. Finally, while typical mechanotransduction studies generally quantify biomarker activity that is indicative of function, it would be desirable to have an LOC that quantifies functional outcomes, including bone formation and bone resorption.

Therefore, there is a need for LOCs that remove the temporal and spatial limitations of cellular interaction of bone tissue, to enable the concurrent study of various bone cell types, while also allowing the quantification (i.e. bone formation and bone resorption) of functional outcomes of bone remodeling. In addition, there is a need for LOCs that may be configured to provide a biomimetic environment for researching bone cell behavior, while minimizing the complex systemic effects associated with typical single cell in vivo systems. In addition, there is a need for LOCs that provide complex information regarding bone tissue remodeling, while controlling those confounding factors that are found within in vivo systems. Furthermore, there is a need for LOCs to investigate the synchronous multicellular interactions that occur during normal bone cell turnover, as well the interactions of bone cells when exposed to the influence of various external stimuli or treatments, including, but not limited to: chemical factors (e.g. drugs), electrical factors, particulates, other cell types, the presence or absence of co-factors, and mechanical loading to quantify functional outcomes of the bone cells, including bone formation and bone resorption.

SUMMARY

It is one aspect of the various embodiments disclosed herein to provide a lab-on-a chip (LOC) device that includes a substrate having one or more wells and at least one groove in fluid communication therewith; and a cap configured to be attached to the substrate, to seal the one or more wells and to seal the at least one groove, such that each sealed groove is defined as a tube; wherein the substrate and the cap are formed of polydimethylsiloxane (PDMS), and the at least one well is coated with collagen.

It is still another aspect of the various embodiments disclosed herein to provide a method of analyzing bone cells using an lab-on-a-chip (LOC) that includes configuring an LOC with an arrangement of a plurality of fluidly coupled wells; providing at least one bone cell type in a first one of the plurality of wells, and at least one bone cell type in a second one of the plurality of wells; and applying a treatment condition to the bone cell types of the first well to generate a conditioned medium (CM) therefrom; flowing the CM to the second well having at least one bone cell type; and quantifying an amount of bone formation or bone absorption that occurs in the at least one bone cell type in the second well in response to the CM.

BRIEF DESCRIPTION OF THE DRAWINGS

The various embodiments disclosed herein will become better understood with regard to the following description, accompanying drawings, and appended claims wherein:

FIG. 5A is diagrammatic image of a microloading platform and osteocyte stimulation, including a microloading platform developed for mechanical tenting of osteocytes to reproducible strain levels, PDMS well design with tracking grid and SEM of osteocytes seeded on PDMS well with tracking grid in accordance with the various concepts and disclosures presented herein;

FIG. 5B is a chart and diagrammatic view showing LDH quantification of cell activity as a function of load type (top), whereby a physiologic load induces significantly greater LDH activity than did physiologic/supraphysiologic or supraphysiologic loads; a physiologic/supraphysiologic load induced significantly greater LDH activity than did a supraphysiologic load; scale bars represent standard errors of the mean in accordance with the concepts of the disclosures presented herein;

FIG. 5C is a chart showing conditioned medium (CM) cytokine activity showing expression (relative to unloaded controls) of biomarkers related to bone cell remodeling, whereby several apoptosis-related markers were identified, and values represent means of three samples in triplicate in accordance with the various concepts and disclosures presented herein;

FIG. 8A is a diagrammatic view of osteoblast characterization, whereby rhodamine phalloidin images with typical MC3T3-E1 cells in culture at days 1, 2 and 16 post-induction are shown in accordance with the various concepts and disclosures presented herein;

FIG. 8B is a diagrammatic scanning-electron microscope (SEM) image showing typical MC3T3-E1 cells in culture in accordance with the various concepts and disclosures presented herein;

FIG. 8C is a diagrammatic image showing tissue cultured (TC) treated LOC wells at 26 days (left) and polystyrene discs from LOC at 49 days (right) post-induction and stained with alizarin red (top) and von Kossa (bottom); whereby the discs measure approximately 5.4 mm in diameter in accordance with the various concepts and disclosures presented herein;

FIG. 8D is a graph showing percentages of disc area covered by alizarin red and von Kossa stains, whereby error bars represent standard errors of the means in accordance with the various concepts and disclosures presented herein;

FIG. 8E is a pair of graphs showing typical EDX of osteoblastic bone nodules in plates at 26 days from uninduced controls (top) and induced MC3T3-E1 cells (bottom), establishing baseline composition; whereby induced samples showed a 12-fold increase in calcium (Ca) and a 7-fold increase in phosphorous (P) over uninduced samples (Ca/P=1.7) in accordance with the various concepts and disclosures presented herein;

FIG. 9A is a diagrammatic image showing osteoclast characterization, whereby a phase image of RAW 264.7 cell 4 days post-induction on tissue culture (TC) treated plate in accordance with the various concepts and disclosures presented herein;

FIG. 9B is a diagrammatic SEM image of osteoclastic resorption on surface of bone wafer at 20 days (cells seeded at 1,000 cells/well) in accordance with the various concepts and disclosures presented herein;

FIG. 9C is a diagrammatic view showing a typical TRAP stain on tissue cultured (TC) treated polystyrene with activity quantification in accordance with the various concepts and disclosures presented herein; and FIG. 9D shows typical bone wafers with pit staining at 20 days within 96-well plates and at 30 days of culture in the LOC; average resorption as determined by toluidine blue surface area staining was 24.9%, 30.4% and 28.7% for cells seeded at 1,000 cells/well and cultured for 20 days, 1,500 cells/well and cultured for 30 days and 56,000 cells/well and cultured for 30 days, respectively; bone wafers measure approximately 6 mm in diameter, and error bars represent standard errors of the means in accordance with the various concepts and disclosures presented herein.

DETAILED DESCRIPTION

Figure 1A:
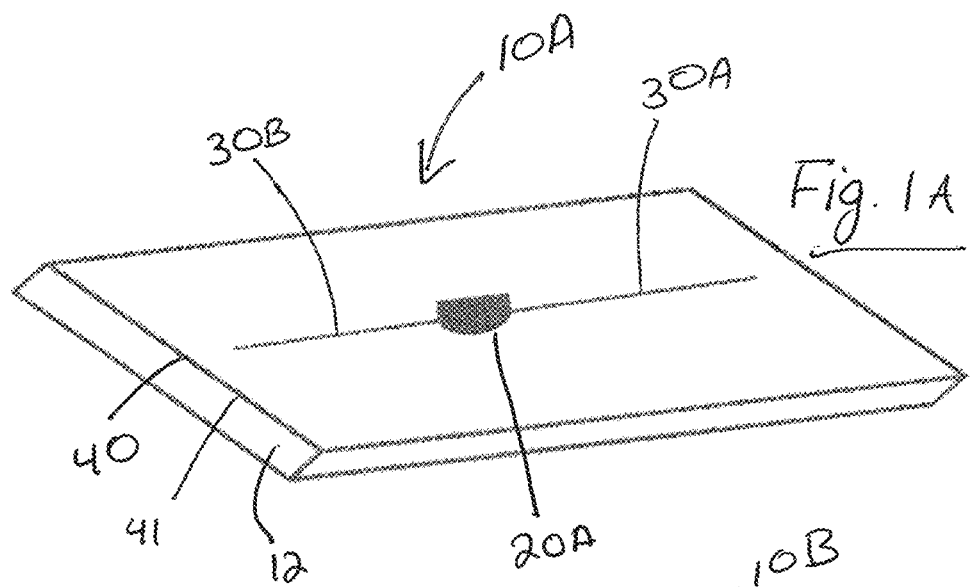
FIG. 1A is a perspective view of an LOC in accordance with the various concepts and disclosures presented herein.
Figure 1B:
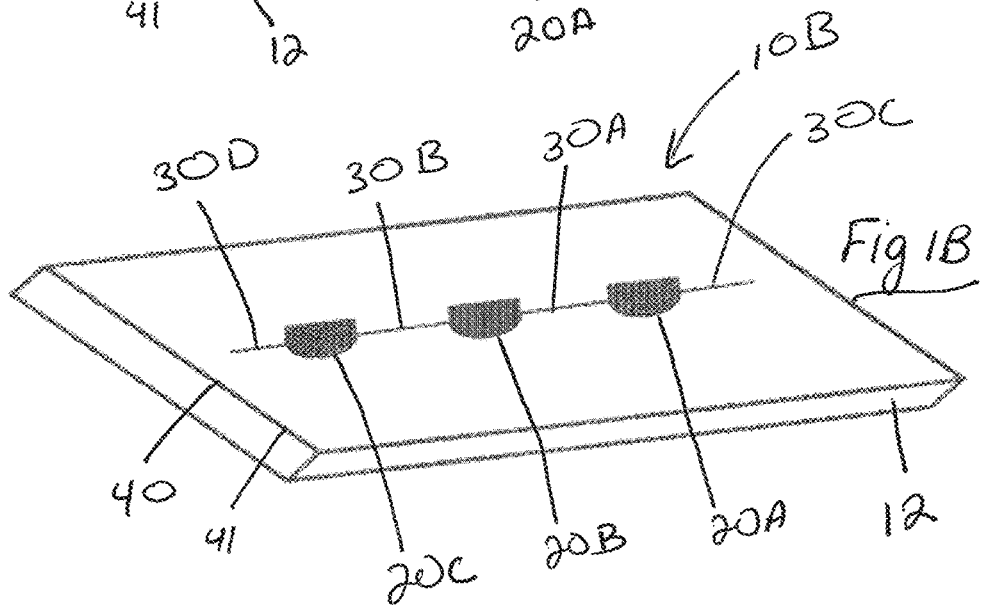
FIG. 1B is a perspective view of another embodiment of the LOC in accordance with the various concepts and disclosures presented herein.
Figure 1C:
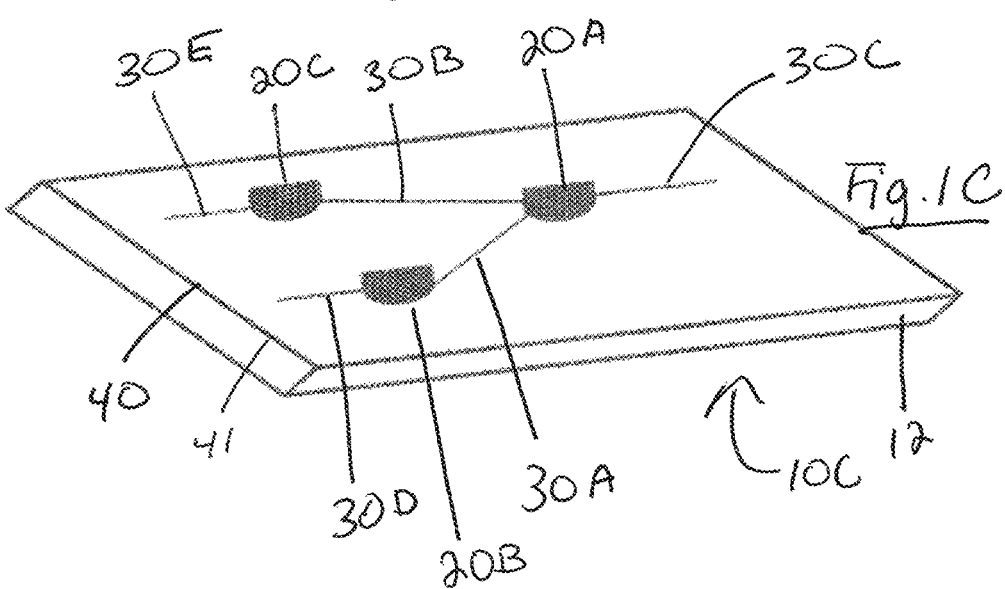
FIG. 1C is a perspective view of another embodiment of the LOC in accordance with the various concepts and disclosures presented herein.

A lab-on-a-chip (LOC) platform for the quantification of multicellular interactions in bone tissue remodeling is disclosed herein in accordance with various embodiments that are each generally referred to by numeral 10, as shown in FIGS. 1-2. In particular, the LOC 10 is configured as a biomimetic environment for the study of functional outcomes, including bone resorption and bone formation, of bone cells, which occur in the presence or absence of various stimuli. Such bone cells utilized by the LOC include, but are not limited to: osteoblasts, bone forming cells; osteoclasts, bone resorbing cells; and osteocytes, mechanosensory cells that are positioned within a bone matrix that sense mechanical stimuli, which resultantly, through chemical signaling, direct osteoblasts and osteoclasts during the bone remodeling process.

The following discussion presents the general features common to all LOCs 10 presented herein, while the various embodiments of the LOC identified as 10A, 10B, 10C and 10D are provided to illustrate the particular manner in which the general LOC 10 may be configured or customized to have any number of wells 20 and tubes 30 to achieve a user's desired research objective. In particular, the LOC 10 includes a substrate 12 formed of polydimethylsiloxane (PDMS). Disposed in the substrate 12 is one or more wells 20 that are fluidly connected to one or more channels or tubes 30 that facilitate the movement of various materials into and/or out of the one or more wells 20. It should be appreciated that the tubes 30 may be formed directly within the substrate 12, or tube 30 may be initially formed as a channel or groove, such that when the substrate 12 is covered by a cap or lid 40 to be discussed, the channel or groove is covered to form the completed tube 30.

In particular, the wells 20 and the channels 30 are covered, so as to be fluidly sealed from the outside environment, by a cap or lid 40 that may also be formed of a PDMS sheet or section. It should be appreciated that in some embodiments, the cap or lid 40 may be removable from the substrate 12 by a user. This sheet forming the lid 40 may be coextensive with the dimension of the substrate 12 of the LOC 10, or may be configured to only cover discrete areas that encompass the wells 20 and the tubes/channels 30. It should also be appreciated that the LOC 10, including one or more of the substrate 12 and lid 40, may be formed using any suitable manufacturing process, including additive manufacturing (AM) techniques, such as sterolithography or three-dimensional (3D) printing for example.

With regard to the one or more wells 20, they may be configured to have any suitable cross-sectional shape, such as a rectilinear shape, a curvilinear shape, or a shape that is a combination of both. For example, in some embodiments, the wells 20 may be spherical, or partially spherical having a truncated surface. Furthermore, in some embodiments, the one or more wells 20 may have a depth measured from the outer surface 41 of the substrate 12 that is proximate to the opening of the well 20 that is approximately 0.5 mm, however any suitable depth dimension may be used, including but not limited to a depth in a range of between about: 0.4 mm to 0.6 mm, 0.3 mm to 0.7 mm, and 0.2 mm to 0.8 mm. In addition, the one or more wells 20 may have a diameter of about 6.5 mm, however any suitable diameter dimension may be used, including but not limited to between about: 5.5 mm to 7.5 mm, 4.5 to 8.5 mm, and 3.5 to 9.5 mm. It should also be appreciated that the one or more of the wells 20 may be optionally coated with collagen material, such as type I collagen (CTI). As such, the wells 20 serve as locations in which one or more bone cell types, including osteocytes, osteoclasts and osteoblasts are located. In addition, various substrate materials may be disposed in the wells 20 that are provided for the bone cells to interact with or to be otherwise carried on. For example, such substrates may include polystyrene or bone tissue, which in some cases may be provided as a chip, disk or wafer for example, but may be provided in any desired dimension or form factor. Moreover, the wells 20 may be configured to include one or more other various co-factors. For example, the co-factors may include, but are not limited to: conditioned medium (CM) (including any soluble signals generated by the bone cells), virus, bacteria, any chemical (such as a drug) or particulate material, as well as any resulting byproduct materials generated from the interaction of the various bone cells. Bone cells may be derived from any source, such as human or animal sources for example, and may include immortalized cell lines, primary cultures or genetically modified cells, as well as combinations thereof. Additional auxiliary cells, such as cancer cells or immune cells, for example, may be added to quantify interactions with bone cells. In some embodiments, the bone cells, substrates and co-factors may be disposed on the one or more wells 20 prior to their being sealed by the lid 40.

With regard to the channels or tubes 30, they may be configured to have any suitable cross-sectional shape, such as a rectilinear shape, a curvilinear shape, or a shape that is a combination of both. In addition, the channels or tubes 30 may be formed as micro-channels, whereby such tube 30 has at least one dimension that is smaller than 1 millimeter in size. For example, in some embodiments, the one or more channels 30 may be configured such that a width dimension is about 300 um and a height dimension is about 400 um. It should be appreciated that the cap of lid 40 is configured with a suitable thickness to enable its puncture by a needle or other sharp instrument to form an access port (not shown) that is in fluid communication with a given tube 30. The access port may have a diameter that is about 1 mm, but may be any other suitable dimension, such as between 0.1 mm to 2 mm for example. The access port may be fluidly coupled to an access tube (not shown) or other conduit to enable the delivery or withdrawal of material from the LOC 10. Thus, in some embodiments, the access port formed in the cap or lid 40 may be utilized to be fluidly coupled to a suitable external pumping or flow mechanism, which is capable of delivering a suitable amount or volume of liquid material, such as bone cells and/or co-factors, into the tube for delivery to one or more of the wells 20. In some embodiments, the pump may include a pico-pump, which is dimensioned to deliver a volume of material, such as liquid material, that is on the order of picoliters. As such, the tubes 30 enable the flow of any desired material into and/or out of the one or more wells 20. For example, the tubes 30 may be used to flow bone cells (osteocytes, osteoclasts, osteoblasts), and/or co-factors through the LOC 10.

In addition, when the LOC 10 is in operable form with the cap or lid 40 placed on the substrate 12 it forms a flexible body of a suitable durometer that is capable of being temporarily deflected or loaded with an applied force, which is imparted to one or more bone cell types disposed in one or more of the wells 20. In other words, the LOC 10 is configured so that it is capable of transferring an applied force or loading to bone cells that are disposed in the wells 20.

With the components of the LOC 10 set forth, which may be configured so that any number of wells 20 may be fluidly connected in any arrangement by any number of tubes 30, a discussion of the particular embodiments of the LOCs 10A-C is presented, with the particular arrangement of the wells 20 and tubes/channels 30 being described. In particular, LOC 10A includes a well 20A that is in fluid communication with auxiliary flow tubes 30A-B. It should be appreciated that auxiliary flow tubes refer to those flow tubes that do not connect two or more wells 20 together. Accordingly, LOC 10A includes a single well 20A, and as such the LOC may be configured for characterization and control purposes during the study of bone cells.

LOC 10B incudes a plurality of wells 20A-C that are arranged in a linear configuration, and which are fluidly coupled in series by a plurality of interconnecting flow tubes 30A-B, while wells 20A and 20C are also coupled to auxiliary flow tubes 30C and 30D, respectively. It should be appreciated that interconnecting flow tubes refer to those flow tubes that connect two or more wells 20 together. That is, well 20A is fluidly coupled to well 20B by interconnecting flow tube 30A, and well 20B is fluidly coupled to well 20C by interconnecting flow tube 30B, whereas well 20A and well 20C are respectively fluidly connected to auxiliary flow tubes 30C and 30D.

Continuing, LOC 10C includes a plurality of wells 20A-C that are arranged in a triangular configuration, whereby well 20A is directly fluidly coupled with well 20B and with well 20C via respective interconnecting flow tubes 30A-B. That is, well 20A is fluidly coupled to well 20B by flow tube 30A, and well 20A is fluidly coupled to well 20C via flow tube 30B, whereas auxiliary flow tubes 30C-E are respectively coupled to wells 20A, 20B and 20C. It should be appreciated that the interconnecting and auxiliary flow tubes are structurally equivalent, however as previously discussed, the interconnecting flow tubes enable the flow of various materials between wells 20, while the auxiliary flow tubes enable the flow of various materials into and/or out of one of the wells 20A-C.

It should be appreciated that while the embodiments discussed herein relate to an LOC using 1-3 wells, the LOC 10 may be configured with any number of wells 20 and flow tubes 30 to enable the performance of a user's desired research objective.

To fabricate the LOC 10, PDMS is used, whereby a 10:1 elastomer base to curing agent (Sylgard™ 184, Dow Corning) ratio is utilized. In particular, the PDMS is mixed, in some cases vigorously, and desiccated. Next, the PDMS is poured into a mold and cured for approximately 48 hours at room temperature to form the substrate 12. As discussed above, the thickness or depth of the wells 20 may be about 0.5 mm, although any suitable thickness or depth may be used. It should also be appreciated that the cap 40 is formed using the same PDMS formulation and molding technique discussed above. In some embodiments, the cap 40 may have a thickness of about 4 mm, although any other thickness may be used, such as between: 1 to 10 mm; 2 to 9 mm, 3 to 8 mm; and 4-7 mm for example.

The wells 20 of the various embodiments of the LOCs 10 may include one or more bone cell types, including: osteocytes, osteoblasts, and osteoclasts may be disposed. In addition to bone cells, one or more co-factors may be included with the cells. Such co-factors include, but are not limited to: growth factors, tissue regenerative agents, soluble signals from bone cells, conditioned medium (CM), liquid materials, solid particulate materials, cells, viruses, and bacteria. In addition, the LOCs 10A-C may be subjected to one or more external forces or external phenomena, including but not limited to: a physical force, such as by out-of-plane distension, electromagnetic radiation, as well as any mechanical or electrical stimulus, or any combination thereof.

Thus, the LOC 10 provides a versatile biomimetic research platform, whereby for example osteocytes may be cultured in one or more wells 20, and then subjected to a force loading, such as by out-of-plane distension of the LOC; or where osteoclasts or osteoblasts are cultured on suitable substrates within one or more wells 20, and evaluated to quantify bone resorption and formation. Accordingly, the functional flexibility of the LOC 10 enables a multitude of bone remodeling interactions, pathways and paradigms to be achieved.

Experimental Section:
I. LOC Platforms

Figure 2A:
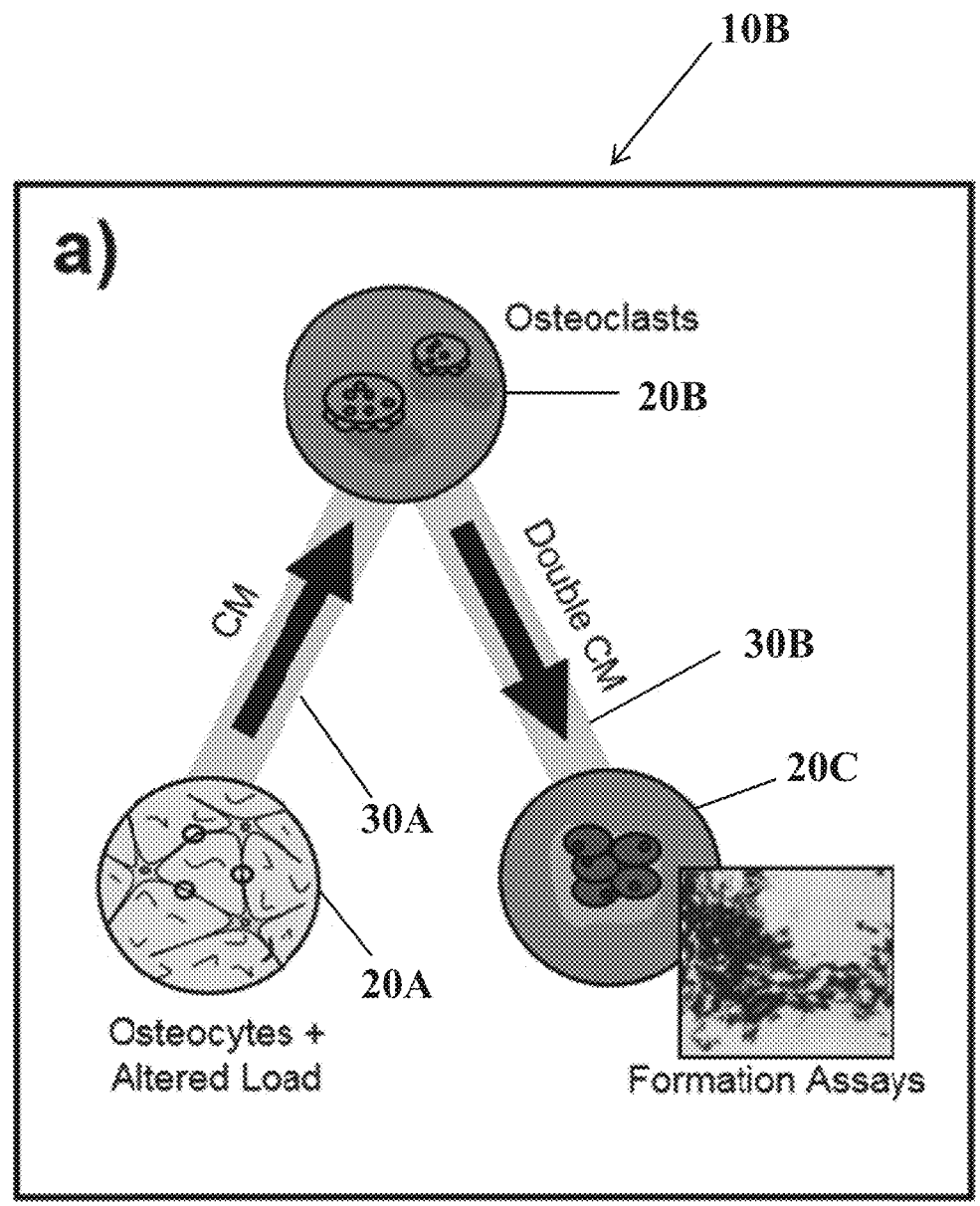
FIG. 2A is a diagrammatic view of another embodiment of the LOC, whereby osteocytes are subjected to an altered mechanical load in accordance with the various concepts and disclosures presented herein.

In view of the LOCs discussed above, various embodiments of the LOCs 10B-D were utilized to carry out the necessary multicellular interactions of bone cells that were necessary to attain a desired research objective. In particular, as shown in FIG. 2A, the LOC 10B discussed above, was configured for the research objective of investigating the effects of osteoclast soluble activity on bone formation. Accordingly, osteoclasts that were disposed in well 20B were exposed to a conditioned medium (CM) that was pumped via tube 30A from well 20A that included mechanically stimulated osteocytes. The soluble signals generated by the osteoclasts in well 20B and the soluble signals from the osteocyte stimulation in well 20A, combined in well 20B to form a double CM, which is then pumped to well 20C. At well 20C, osteoblasts are provided, which are cultured on a tissue culture (TC) treated polystyrene disc are exposed to the double CM. Finally, the effects of these soluble signals on osteoblast bone formation in response to the double CM was then quantified using any suitable assay.

Figure 2B:
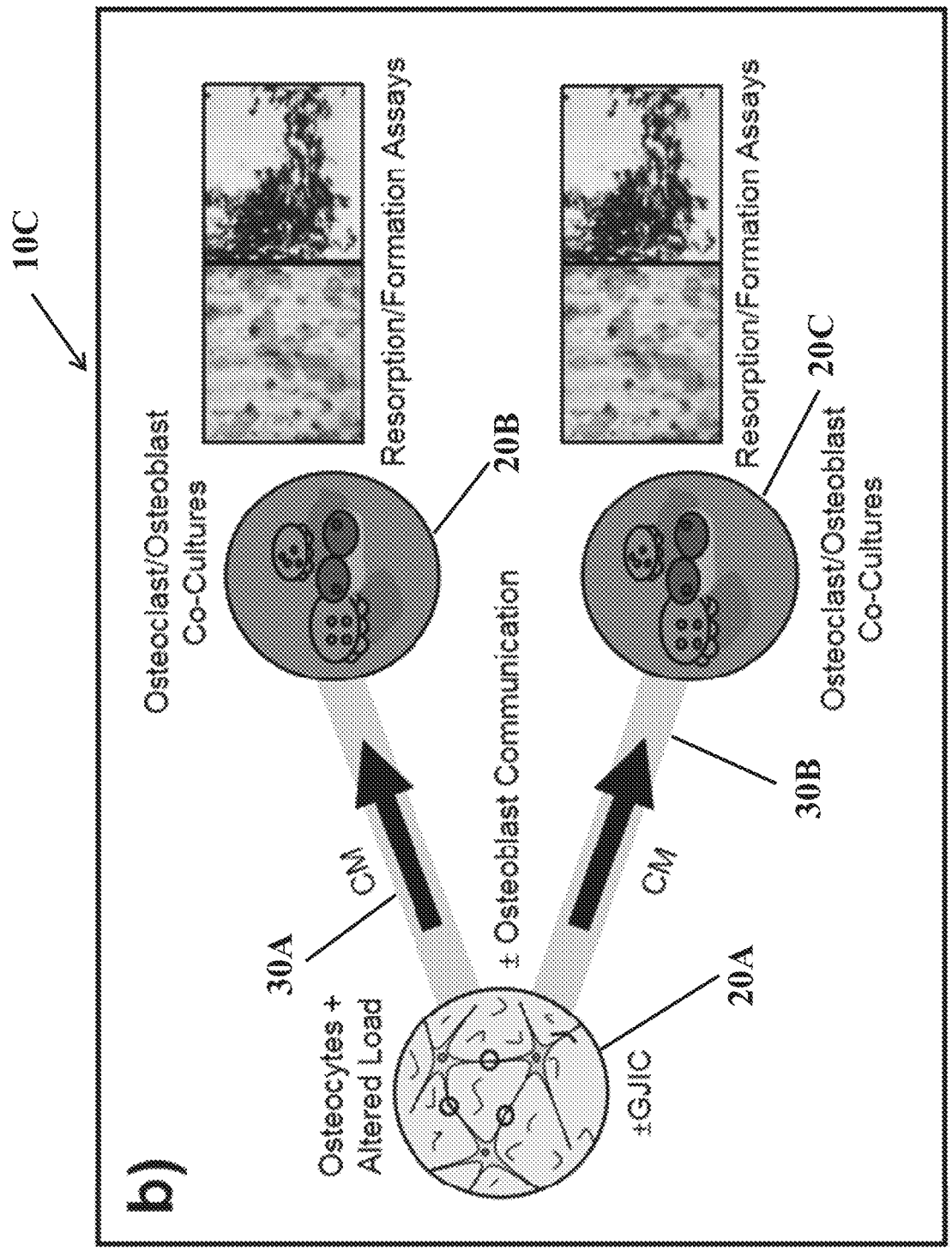
FIG. 2B is a diagrammatic view of another embodiment of the LOC, whereby osteocytes are subjected to an altered mechanical load in either the presence or the absence of gap-junction intercellular communication (GJIC) in accordance with the various concepts and disclosures presented herein.

LOC 10C, as shown in FIG. 2B, was configured for the research objective of investigating the direct effects of stimulated osteocyte CM on net bone resorption and bone formation. In particular, co-cultures were exposed to CM from mechanically stimulated osteocytes with bone resorption and formation being quantified. In particular, osteocytes in well 20A were subjected to an altered load, either in the presence or absence of gap junctional intercellular communication (GJIC). Next, the conditioned medium (CM) generated by the osteocytes at well 20A was pumped through tubes 30A and 30B to two separate co-cultures of osteoclasts/osteoblasts in respective wells 20B and 20C. In particular, the culture in well 20B is configured whereby osteoblast communication is enabled, while the culture in well 20C is configured whereby osteoblast communication is inhibited. Finally, the co-cultures in wells 20B and 20C were evaluated to quantify the amount of bone resorption and bone formation that occurs. Accordingly, LOC 10C allowed the comparison of the results of the effects of the CM on the osteoclast/osteoblast co-cultures, so that the role of the soluble signals as compared to direct cell contact in mechanically induced bone remodeling can be investigated. In addition, the LOC 10C can be used to evaluate contact-dependent cell-cell communication via gap junctional intercellular communication (GJIC). Given the availability of gap junction inhibitors (topical additives) and knock-down models, such configurations can be used to investigate GJIC-intact or GJIC-inhibited environments to determine the contribution of GJIC to bone cell contact synergy.

Figure 2C:
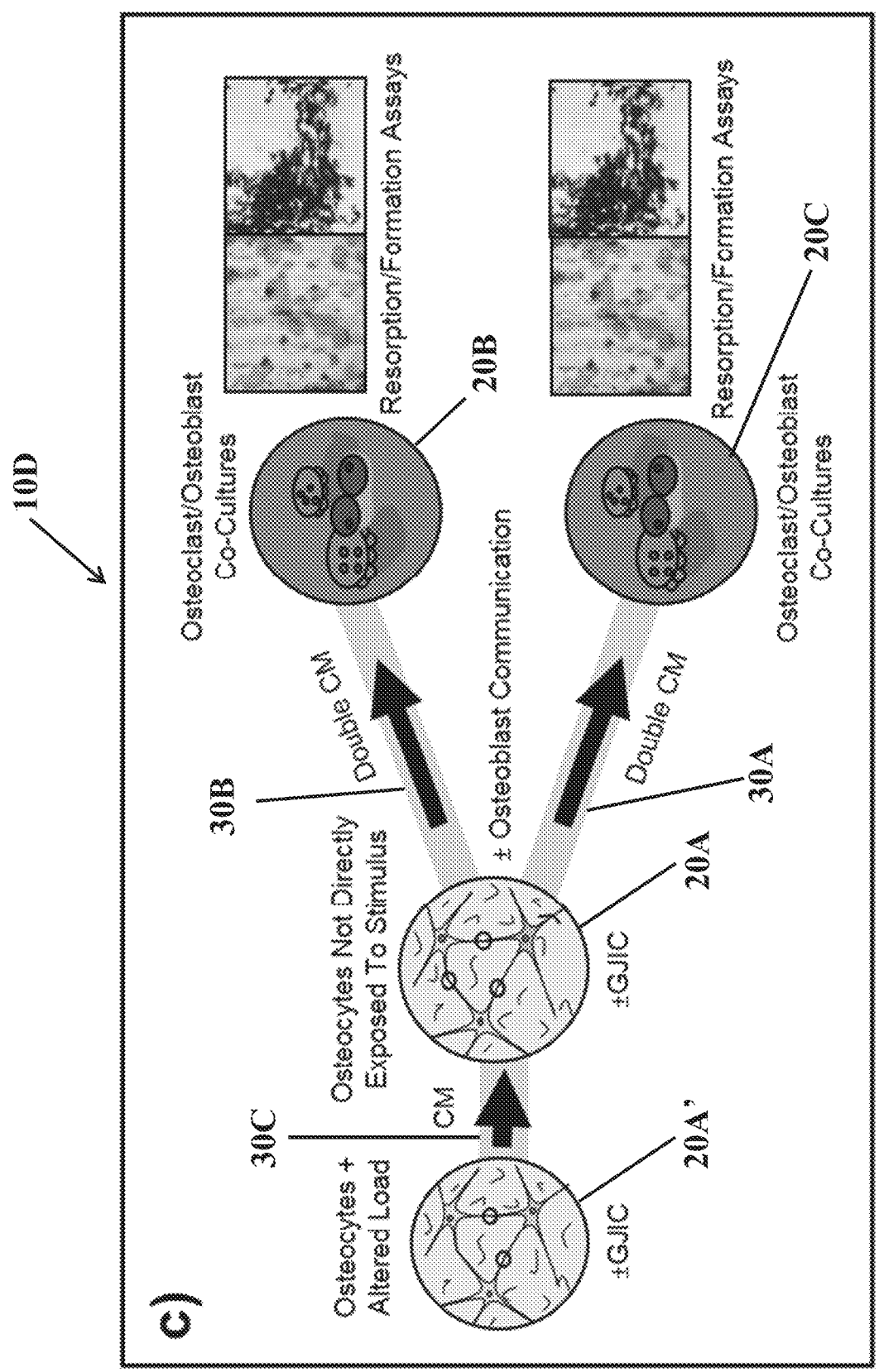
FIG. 2C is a diagrammatic view of another embodiment of the LOC, whereby osteocytes are subjected to damage signals generated by other stimulated osteocytes in presence or absence of GJIC in accordance with the various concepts and disclosures presented herein.

In the embodiment shown in FIG. 2C, an LOC 10D is configured in a manner similar to that of LOC 10C, but including an additional well 20A' to study the relay of damage signals from stimulated (e.g. force loaded, unloaded, particles, cytokines) osteocytes to unstimulated osteocytes. Accordingly, a determination can be made as to whether the directly stimulated osteocytes or those neighboring cells sensing damage signals carry most of the responsibility in mediating remodeling. In particular, unstimulated osteocytes in well 20A are exposed to CM delivered via tube 30C from mechanically damaged (i.e. overloaded) osteocytes that are provided in well 20A'. The indirectly stimulated osteocytes in well 20A, either in the presence or absence of gap junctional intercellular communication (GJIC), generate soluble signals that together with the soluble signals from the well 20A' form a double CM. This double CM is then delivered to co-cultures of osteoblasts and osteoclasts that are in respective wells 20B and 20C. In particular, the culture in well 20B is configured whereby osteoblast communication is enabled, while the culture in well 20C is configured whereby osteoblast communication is inhibited. Finally, the co-cultures in wells 20B and 20C were evaluated to quantify the bone resorption and bone formation that occurs.

II. Materials and Methods

1. Approach

Two LOCs were characterized: a mechanically loadable LOC which has been previously described and a functional activity LOC. Significant characterization work was completed to demonstrate the ability to fabricate a mechanically loadable device from PDMS using material property testing and parametric modeling. This work illustrated that osteocytes directly contacting the collagen-coated PDMS within the LOC were not phenotypically altered on the polymer and that cell activity can be correlated to substrate location and strain. The initial goal was to investigate short-term exposure of osteocytes to force overload and damage, as well as its effects on bone remodeling. We have previously identified osteocyte loading ranges that are physiologic ($\leq 10\%$ substrate strain), physiologic/supraphysiologic (overload-inducing) and supraphysiologic (death-inducing) using mechanical testing, finite element analysis, digital image correlation techniques and quantification of osteocyte activity (e.g., viability) as a function of load. For example, we discovered lactate dehydrogenase (LDH)—a marker of cell viability—activity was significantly decreased following 15% (physiologic/supraphysiologic) loading. It was demonstrated that the loadable platform can be used to study single cell type responses and is amenable to immunochemistry, imaging—fluorescence and scanning electron microscopy (SEM)—and protein analysis. An initial proof of concept was completed by studying the effects of stimulated osteocytes on bone remodeling. Osteocytic factors were analyzed, and the effects of CM on bone formation were quantified. Additionally, studies were performed to characterize osteoclasts and osteoblasts with the functional activity LOC and to verify they form bone on tissue culture (TC) treated polystyrene discs, and that they resorb bone on wafer inserts placed within the LOC device. Accordingly, the feasibility and fidelity of the LOC was confirmed, and was demonstrated to facilitate mechanical loading and bone remodeling.

2. Verification of Osteocyte Morphology and Phenotype on PDMS in Mechanically Loadable LOC MLO-Y4 osteocytes were seeded at a density of $10^4$ cells/cm$^2$ within T-25 culture flasks, maintained at 5% CO2 and 37° C. and grown to 85-90% confluence in minimum essential alpha medium (MEMa, Gibco) supplemented with 5% calf serum, 5% fetal bovine serum (FBS, Hyclone) and 1° A penicillin/streptomycin (Invitrogen). Cells were seeded at $2*10^4$ cells/cm$^2$ on PDMS wells coated with CTI (BD Bioscience) in 0.2 M acetic acid (Sigma) at a concentration of 5 μg/cm$^2$ for 1 hour prior to rinsing in DPBS solution with calcium and magnesium (Hyclone). Osteocyte proliferation on PDMS was previously verified over 120 hours and compared to proliferation on glass. LDH activity was verified at each time point (4, 24, 48, 72, 96, 120 hour). Immunochemistry demonstrated the expression of key osteocyte markers, including dickkopf-1 (Dkk-1), receptor activator of nuclear factor kappa-B ligand (RANKL) and the gap junction protein Cx43 (York et al., 2015). Briefly, cells on CTI-coated PDMS were washed in PBS, fixed using a paraformaldehyde solution at room temperature for 15 min. and permeabilized for 10 min. in a PBS solution containing 0.1% Triton X-100. A primary antibody was added in 1:50 or 1:100 ratios in 1% bovine serum albumin (BSA) solution and incubated overnight at 4° C. Cells were washed in PBS, secondary antibody was added in a 1:500 ratio in 1% BSA solution and incubated at room temperature for 1 hour. Cells were washed, mounted using PermaFluor™ mountant, coverslipped and imaged. To visualize the actin cytoskeleton, rhodamine phalloidin with nuclear DAPI staining was completed. Following fixation in a 4% formaldehyde solution for 10 min., cells were rinsed in PBS and permeabilized in 0.2% Triton X-100 in PBS. Rhodamine phalloidin was added to the cells in a 2.5% v/v solution to 0.1% BSA in PBS. Following 20 min of incubation at room temperature, cells were washed in PBS. They were mounted using Vectashield with DAPI and imaged. SEM was also completed to verify morphology. For SEM, cells were fixed in a 2% glutaraldehyde, 2% paraformaldehyde solution in PBS for 15 min. and washed with PBS and distilled water. Dehydration was performed over a period of 20 min., whereby the cells were dehydrated in 25% ethanol increments until immersed in 100% ethanol. Cells were critical point dried, sputter coated and imaged using SEM.

3. Use of Mechanically Loadable LOC 3.1 Mechanotransduction Tool

To demonstrate the use of the force loadable LOC 10 as a mechanotransduction tool, osteocytes were maintained on the CTI-coated PDMS wells 20 within the device for a minimum of 96 h before loading. Bone Cells were then exposed to 15 min. of out-of-plane distention using a microactuated loading machine developed in-house and incubated for 90 min. Differential activity was then quantified. An alignment system was developed to enable precise manipulation of the LOC 10 and cell tracking for correlating substrate strain with cellular activity. Based upon significant pilot characterization, physiologic loading 0% strain), physiologic/supraphysiologic loading (15-19% strain) and supraphysiologic loading (19-34% strain) were generated by distending the platen to 3,804 µpm, 5720 µm and 7240 µm, respectively for a given well base thickness. Viability was quantified as a function of platen displacement with LDH staining and image analysis. CM was collected for cytokine quantification with ELISA or added to osteoblast cultures to quantify the effects of mechanical stimulation of osteocytes on bone formation.

As discussed, LDH activity was completed to quantify cellular activity following loading. Osteocytes were washed with HBSS, then incubated in a reaction solution containing 5% Polypep (Sigma-Aldrich) base solution, 2 mM gly-gly (Sigma-Aldrich), 1.75 mg/ml nicotinamide adenine dinucleotide (NAD, Fluka), 60 mM lactic acid (Sigma-Aldrich), 3 mg/ml nitroblue tetrazolium (Sigma-Aldrich) and HBSS at a pH of 8.0. Following 1 hour of incubation, cells were washed with distilled water and fixed in 4% paraformaldehyde overnight. Following fixation, the cells were washed with distilled water and mounted with an aqueous mounting solution (VECTASHIELD®) and coverslips. Next, imaging and quantification were performed.

ELISA panels (RayBiotech, Inc.) were used to analyze the concentration of soluble factors within the CM after mechanical loading. Cytokine-specific antibodies were bound to a glass slide and incubated with the CM to be analyzed. To ensure specific detection, antibodies bound to biotin were added to the CM to form cytokine-antibody-biotin complexes after incubation. Streptavidin labeled with Cy3 was added in a third incubation. Cy3 was detected using a laser scanner and levels were compared to standards, allowing for the detection and quantification of cytokines. Sandwich ELISA panels were run three times in triplicate with medium collected and averaged, generating an average response across all runs.

3.2 Remodeling Tool

To demonstrate the strength of the LOC platform in quantifying the net result of a bone's multicellular interactions, soluble effects of osteocyte loading on osteoblast bone formation were quantified. In these experiments, CM that was generated following loading from physiologic 0% strain) or physiologic/supraphysiologic (15%-19% strain) conditions were collected and used. During feedings, CM was introduced to osteoblast cultures as a 10% volume every three days in 50% volume replacements. All CM was generated in the osteocyte loading studies described above to verify initial consistency. Osteoblastic mineralization was assessed at day 26 using alizarin red staining and extraction, von Kossa staining and EDX. Following alizarin red staining, extraction was performed by adding 50 µL/cm$^2$ of 10% acetic acid to each well 20. Plates were placed on a benchtop shaker and incubated at room temperature overnight. Cells and stain were scraped from each well, pipetted into 1.5 ml tubes and then heated at 85° C. for 10 min. Samples were then transferred to ice for 5 min. and centrifuged at 18,000×g on a tabletop microcentrifuge for 20 min. Finally, the supernatant from each sample was pipetted into a microplate in triplicate. Samples, standards and blanks were read at 405 nm using a microplate reader, and absorbance values were converted to concentrations of alizarin red.

4. Design and Fabrication of Functional Activity LOC

A mask was fabricated to accommodate three configurations of a functional activity LOC: a single well (10A), a three-well linear arrangement (10B) and a three-well triangular arrangement (10C). The mask was designed in AutoCad™ and fabricated using Prototherm 12120 high-resolution stereolithography in a 0.05 mm build. A Plexiglass box with leveling screws in a tripod configuration was machined in-house to hold the mask (15.24 cm×15.24 cm). PDMS was chosen as the material for the LOCs 10A-C. A 10:1 elastomer base to curing agent (Sylgard 184, Dow Corning) ratio was used to make PDMS, which was vigorously mixed and desiccated. PDMS was poured into the mold and cured for 48 hours at room temperature to make bases. Given the intended mechanical studies, well thicknesses of 0.5 mm was selected to avoid tearing the polymer upon loading. TC treated polystyrene discs were inserted into the LOC 10A-C wells that were to contain osteoblasts and adhered to the wells with uncured PDMS prior to sealing the LOC 10A-C chip with the PDMS lid 40. Bone wafers were inserted into the LOC wells 20 that were to contain osteoclasts; they were also adhered to the wells with PDMS. PDMS sheets, or lids, ~4.0 mm thick were made as described above; access holes were bored through the lids using a biopsy punch 1 mm in diameter. The PDMS bases/substrates 12 and lids 40 were plasma oxidized for 30 s using a medium RF power setting (Plasma Cleaner, Harrick Plasma). One base/substrate 12 and one lid 40 per LOC were fused and baked at 65° C. for 10 min. Angled dispensing tips (18 Gauge, 0.5 in, 90°) were inserted into access holes within the lids 40, and epoxy was used to stabilize the tips. They were then attached to silicone tubing (1⁄32" ID). At the opposite end of each tube, an 18 Gauge needle and syringe were attached. The syringes were hooked up to a picopump (Pico Plus, Harvard Apparatus) for administration of liquids at 2 ml/h. Sterile liquids were pumped into the wells and channels of the devices. These included 70% ethanol, Hanks' Balanced Salt Solution (HBSS) (for LOCs containing bone wafers) and distilled water. Osteoblasts were seeded using the picopump onto TC treated polystyrene discs and osteoclasts onto bone wafers within wells of the LOCs. All cells were maintained within LOCs at 5% $CO_2$ and 37° C. for appropriate lengths of time prior to analysis. Feedings were administered every 3 days by use of the picopump. While some cells grew within channels 30, this was curtailed by the geometry of the device. Channels were small enough so that cells preferred to stay within wells 20, where they could proliferate and spread appropriately. Additionally, movement of cells from wells into channels 30 was decreased by use of the low flow rate—2 ml/h—during feedings. For analysis, PDMS lids were removed; as PDMS bonding is permanent, a scalpel was used to access wells 20. Osteocytes were analyzed directly in the wells 20, while discs and bone wafers were removed for osteoblast and osteoclast assays.

5. Verification of Osteoblast Bone Formation in Functional Activity LOC

Preliminary characterizations were performed in TC treated 96-well plates (LOCs) or polystyrene discs for confirmation of typical morphology, osteoblast differentiation and mineralization. MC3T3-E1 preosteoblasts (ATCC) were seeded at a density of 2,500 cells/cm$^2$ and grown to 100% confluence in MEMa supplemented with 10% FBS and 1% penicillin/streptomycin. Cells were maintained at 5% CO2 and 37° C. Cells were induced to differentiate into osteoblasts at 100% confluence with a cocktail containing 50 µg/ml L-ascorbic acid and 10 mM β-glycerophosphate in culture medium. Cells were fed by 50% media replacements every 3 days for 26 days. To verify osteoblastic morphology, rhodamine phalloidin with DAPI staining was completed over the course of the culture period, and SEM was completed using methods previously described. At 26 days, bone formation was quantified with alizarin red and von Kossa staining. Elemental composition was determined by energy-dispersive X-ray spectroscopy (EDX). For alizarin red staining, cells were formalin fixed, stained with alizarin red dye solution for 30 min, washed and imaged. Percent area covered by bone formation was determined using NIH ImageJ. Additionally, concentration of alizarin red dye extracted was performed by adding 10% acetic acid to culture wells and incubating overnight at room temperature. Cells were scraped and heated at 85° C. for 10 min prior to centrifugation. Absorbance was measured at 405 nm using a microplate and a standards range of 15.7 µM to 2 mM. For von Kossa staining, cells were fixed in 4% paraformaldehyde in PBS. A 5% silver nitrate solution was added, and cells were exposed to UV light for up to 60 min. Imaging followed, and percent area covered by bone formation was determined using ImageJ. For SEM/EDX, cells were fixed in a 2% glutaraldehyde, 2% paraformaldehyde solution in PBS for 15 min and washed with PBS and distilled water. Dehydration was performed over a period of 20 min; cells were dehydrated in 25% ethanol increments until immersed in 100% ethanol. Cells were critical point dried, sputter coated and imaged using SEM. EDX was performed in conjunction with SEM using Genesis software, EDAX. Sputter coating was not performed on EDX samples. Within the LOCs, MC3T3-E1 preosteoblasts were seeded onto TC treated polystyrene discs (~5.4 mm ϕ)) at a higher density of 10,000 cells/cm$^2$ to account for loss of cells within silicone tubing. Cells were cultured as described above. Cells were induced to differentiate and fed every 3 days by 100% media replacements for 49 days. Bone formation was verified by alizarin red and von Kossa staining as described above and quantified with ImageJ.

6. Verification of Osteoclast Bone Resorption in Functional Activity LOC

Figure 3:
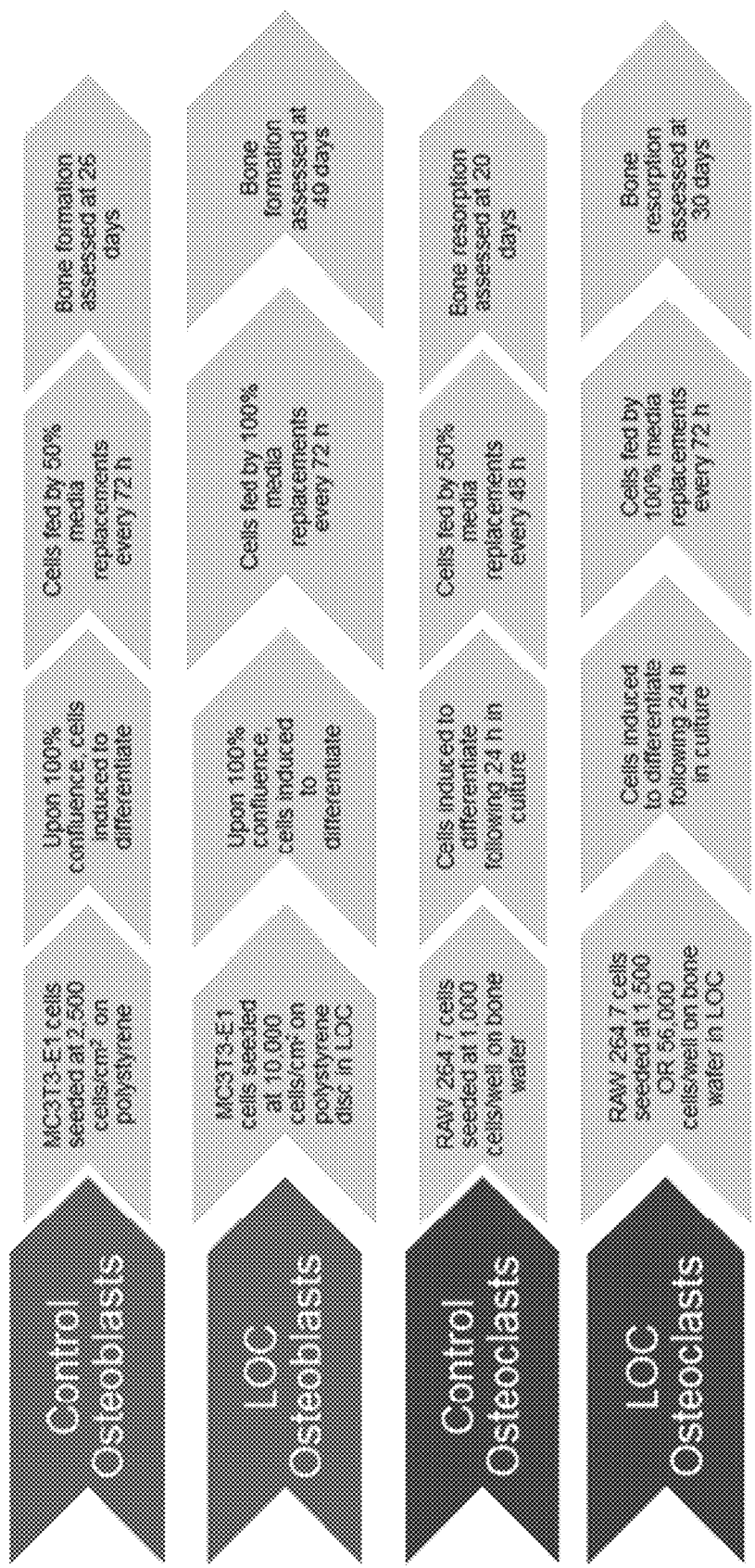
FIG. 3 is a chart showing a cell culture timeline providing seeding densities, substrates, differentiation inductions, feedings and functional activity assessments for control and LOC conditions in accordance with the various concepts and disclosures presented herein.
Figure 4A:
FIG. 4A is a diagrammatic image showing osteocyte characterization, including rhodamine phalloidin staining of MLO-Y4 osteocytes in accordance with the various concepts and disclosures presented herein.
Figure 4C:
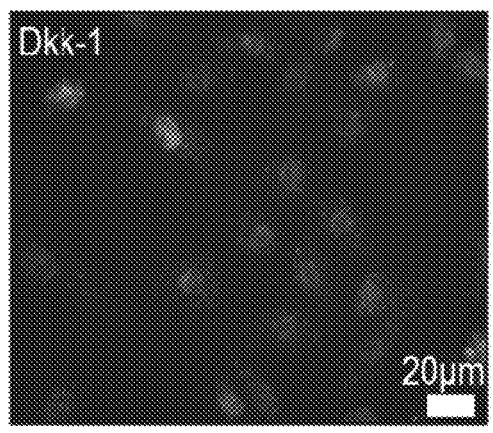
FIG. 4C is a diagrammatic image showing osteocyte characterization including immunocytochemistry staining of osteocyte protein, Dkk-1, in accordance with the various concepts and disclosures presented herein.
Figure 4D:
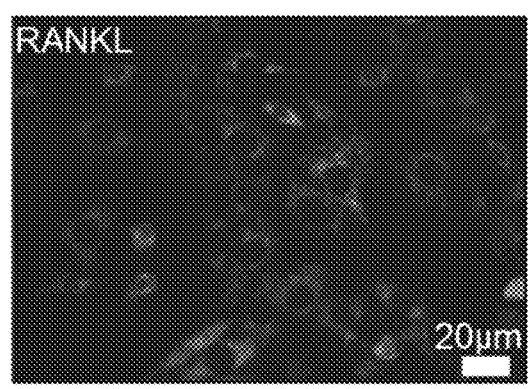
FIG. 4D is a diagrammatic image showing osteocyte characterization including immunocytochemistry staining of osteocyte protein, RANKL and the gap junction protein, in accordance with the various concepts and disclosures presented herein.
Figure 4B:
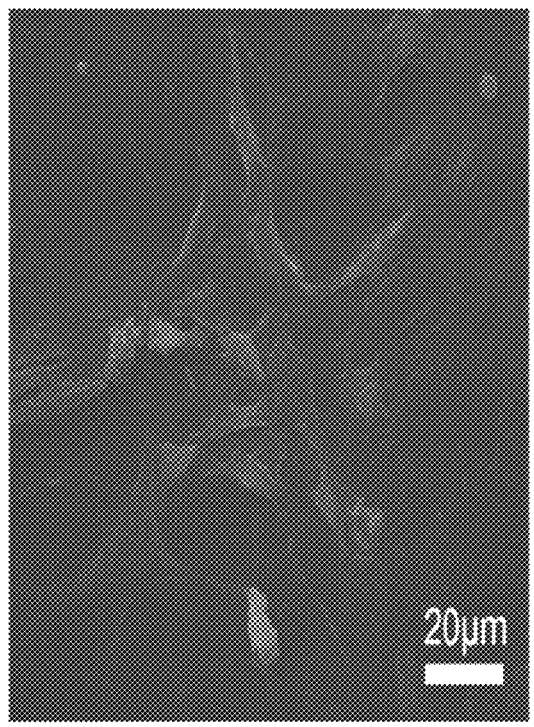
FIG. 4B is a diagrammatic image showing osteocyte characterization including an SEM (scanning electron microscope) image with typical MLO-Y4 osteocytes with dendritic processes in accordance with the various concepts and disclosures presented herein.
Figure 4E:
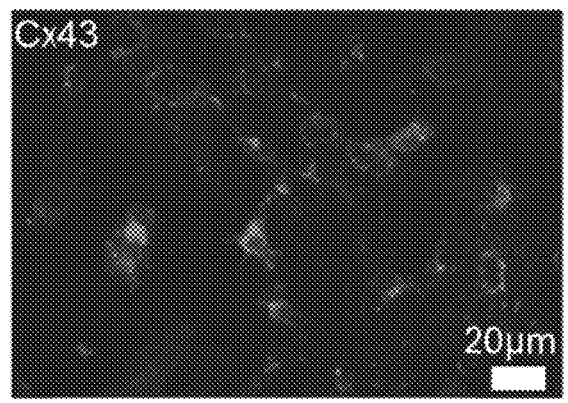
FIG. 4E is a diagrammatic image showing osteocyte characterization including immunocytochemistry staining of osteocyte protein, Cx43, in accordance with the various concepts and disclosures presented herein.

Preliminary characterizations were performed on TC treated polystyrene or bovine bone wafers in 96-well plates (LOCs) for confirmation of typical osteoclast morphology, osteoclast formation and bone resorption. RAW 264.7 preosteoclasts (ATCC) were seeded onto TC treated polystyrene or bone wafers (~6 mm ϕ) at a density of 1,000 cells/well in Dulbecco's modified eagle medium supplemented with 10% FBS and 1% penicillin/streptomycin. Cells were maintained at 5% $CO_2$ and 37° C. Cells were induced to differentiate into osteoclasts at 24 h with a cocktail containing 120 ng/ml RANKL (R&D Systems) in culture medium. Cells were fed by 50% induction medium replacements every 2 days for 4, 5, 10 or 20 days. To verify cell fusion, typical morphology and tartrate-resistant acid phosphatase (TRAP) expression of cells cultured on polystyrene, TRAP stains and activity assays were performed at days 4, 5 and 10. Cells were fixed in 10% neutral buffered formalin and incubated in a solution of 50% methanol and 50% acetone for 3 min at room temperature. TRAP activity substrate (solution of sodium acetate, sodium tartrate and para-nitrophenylphosphate) was added, and cells were incubated at 5% $CO_2$ and 37° C. for 1 h. Following incubation, 100 µl of TRAP activity substrate from each sample were mixed with 50 µl 1 M NaOH, and microplate readings were taken at 405 nm. For TRAP staining, a commercially-available kit, 387A (Sigma Aldrich), was used. Cells were stained in a solution containing sodium nitrite, fast garnet, napthol and tartrate and imaged. Bone resorption was quantified with wafer pit staining at 20 days. Osteoclasts were removed from the wafers by 30 min. of sonication and gentle cleaning with a cotton swab. The wafers were submerged in a toluidine blue solution for 2 min and rinsed briefly with distilled water. Imaging and determination of wafer area covered by resorption followed; quantification was performed by use of ImageJ. SEM verified that wafer regions stained with toluidine blue indicated functional resorption. Within the LOCs, RAW 264.7 preosteoclasts were seeded onto bone wafers at higher densities—1,500 cells/well and 56,000 cells/well—to account for loss of cells within silicone tubing. They were cultured and induced to undergo osteoclastogenesis as described above and fed by 100% induction medium replacements every 3 days. Given results of preliminary work (not shown) indicating that cells within LOCs take 50% longer to resorb efficiently, osteoclasts were cultured for 30 days in the LOC chips. Bone resorption was verified by toluidine blue staining and quantified with ImageJ. A timeline summarizing cell culture of osteoclasts and osteoblasts with control and LOC conditions is given in FIG. 3.

7. Statistics

For characterizations and experiments, D'agostino and Pearson tests were run to determine normality. Raw data were summarized by means with standard errors of the means. Analysis of continuous data was completed with ANOVA (parametric) or Mann Whitney U (nonparametric) techniques. Post-hoc comparisons of specific groups were made using the Tukey (parametric) or Bonferroni (nonparametric) methods. All analyses were completed with Instat (GraphPad). Characterizations and experiments were conducted a minimum of three times in triplicate, except for osteocyte CM studies on osteoblast bone formation given limited CM.

III. Experimental Results

1. Verification of Osteocyte Morphology and Phenotype on PDMS in Mechanically Loadable LOC Given that little work has been completed quantifying the effects of PDMS on osteocyte function, comprehensive characterization studies were performed. It has been previously demonstrated that growth and proliferation on CTI-coated PDMS is not significantly different from that on CTI-coated glass. As shown in FIGS. 4A-E, MLO-Y4 osteocytes on CTI-coated PDMS display the anticipated dendritic morphology. Rhodamine phalloidin and DAPI stains (FIG. 4A) reveal extensive cytoskeletal arrangement of actin filaments, and SEM imaging (FIG. 4B) shows that by 72 hours in culture, characteristic osteocyte morphology is observed. This correlates with the observation that coating and time in culture are required for MLO-Y4 cells to take on the osteocyte morphology. It was found that this consistently occurs by 72 hours; and thus, osteocytes are plated a minimum of 72 hours prior to experimentation. Immunocytochemistry (FIGS. 4C-E) further corroborates the presence of known proteins critical to osteocyte function, including Dkk-1, RANKL and Cx43.

2. Use of Mechanically Loadable LOC
2.1. Mechanotransduction Tool

Mechanotransduction studies employed a loading device and cell tracking system. A loading platform fabricated in-house is shown in FIG. 5A. Briefly, the microactuator raises a plunger that applies out-of-plane distention to the PDMS well, which is shown as part of a single-well LOC chip. A tracking system was developed and validated and enables bone cell strains (substrate strains) to be quantified as functions of grid location and actuator displacement (data not shown). To track positional reference, an alphanumeric grid was incorporated into the osteocyte PDMS well. Following characterization, actuator displacements generating physiologic (≤10% strain), physiologic/suparphysiologic (15-19% strain) and supraphysiologic (19-34% strain) loads were determined and used for all subsequent studies. For viability assessment, LDH was quantified in osteocytes subjected to 15 min. of physiologic, physiologic/supraphysiologic or supraphysiologic loading in intact and inhibited GJIC environments. As shown in FIG. 5B, 15 min of physiologic/supraphysiologic loading decreased cell activity by 14% over physiologic stimulation, and 15 min. of supraphysiologic loading decreased cell activity by 21% over physiologic stimulation. Interpreting the supraphysiologic loading as essentially indicative of cell death, further work with this load was not pursued. Results demonstrate that the LOC platform can be used to quantify the behavior of a single cell type as a function of load, not unlike standard mechanotransduction models. Further, they reinforce the importance of a role for GJIC in the osteocytes' response to mechanical loading, and they illustrate that short-term loading can be effectively administered in the LOC chip.

Using ELISA cytokine panels, we identified over 40 cytokines that were altered under short-term osteocyte loading. Although not an exhaustive list, several of the factors are identified in FIG. 5C, and some offer novel targets for further study. As shown in the color map, green colors indicate a percent increase, and red colors represent a percent decrease over unloaded controls. Percent changes were calculated from three readings, each of which was pooled from three identical treatment wells. Neural cell adhesion molecule 1 (NCAM-1), secreted frizzled related protein 3 (SFRP-3), decorin, ciliary neurotrophic factor (CNTF), serum amyloid A (SAA) and interleukin 1-receptor 3 (IL-1r3) were elevated by short-term physiologic loading. These findings were consistent with observations in previous studies. For example, NCAM-1 potentially curtails bone matrix formation, while SFRP-3 is a negative regulator of Wnt, and CNTF regulates trabecular and cortical bone in a sex-dependent manner. Decorin is known to modulate collagen fibril formation, and SAA inhibits RANKL-induced osteoclast formation. Cytokine decrease under physiologic load was observed with macrophage migratory inhibiting factor (MIF) and extracellular matrix metalloproteinase inducer (EMMPRIN). MIF is associated with bone loss in osteoporotic women, and EMMPRIN has been proposed to be involved in collagen breakdown and bone resorption. The identification of remodeling-related cytokines is consistent with the findings that short-term physiologic stimulation increased bone formation, while physiologic/supraphysiologic stimulation associated with damage reduced formation. These cytokines offer many opportunities for further study using the LOC.

2.2. Remodeling Tool

Figure 6A:
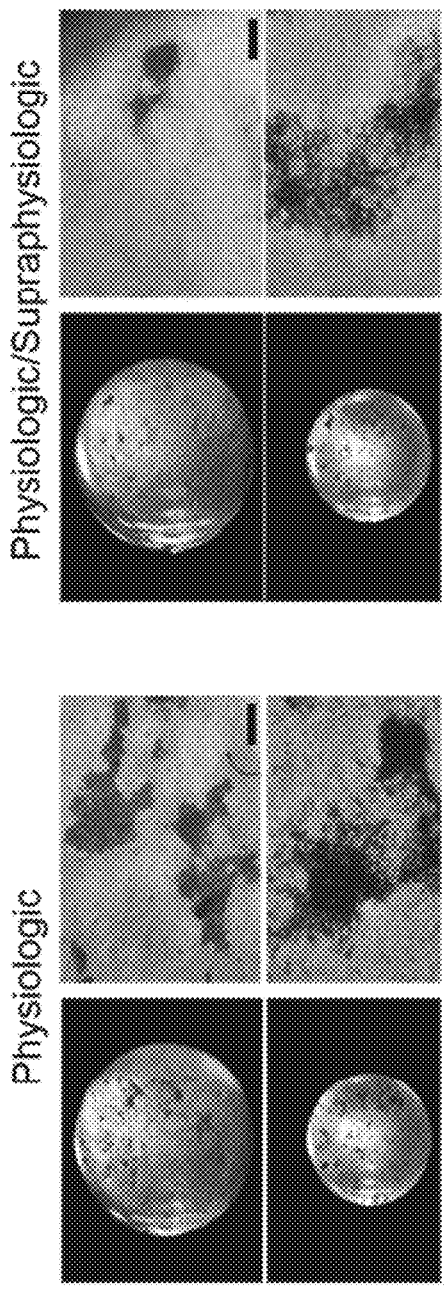
FIG. 6A is a diagrammatic view showing bone formation as a function of osteocyte loading, in which a conditioned medium (CM) from the physiologic loading induced increased bone formation (left) by osteoblastic cells in comparison to CM from physiologic/supraphysiologic loading (right); alizarin red and von Kossa stains were performed for each plate corresponding to both loading conditions; scale bars on the alizarin red (top) and von Kossa (bottom) images measure 500 μm and 200 μm, respectively in accordance with the various concepts and disclosures presented herein.
Figure 6D:
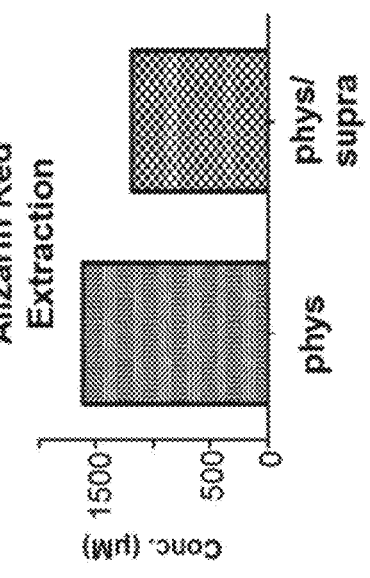
FIG. 6D is a chart showing a physiologic study of bone cells, whereby alizarin red extraction showed a 36% increase in dye concentration compared to physiologic/supraphysiologic loading studies of bone cells, and percent area increases were 18% as indicated by alizarin red stains (FIG. 6B), and were 21% as indicated by von Kossa stains (FIG. 6C), whereby a sample size of at least 3 is represented in accordance with the various concepts and disclosures presented herein.
Figure 6C:
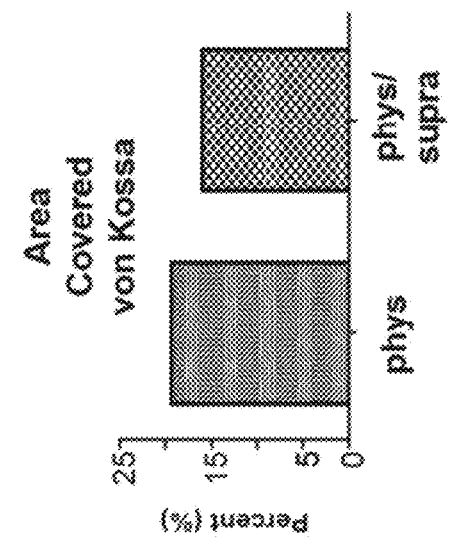
FIG. 6C is a chart showing a physiologic study of bone cells, whereby von Kossa stains were used to compare physiologic/supraphysiologic loadings of bone cells in accordance with the various concepts and disclosures presented herein.
Figure 6B:
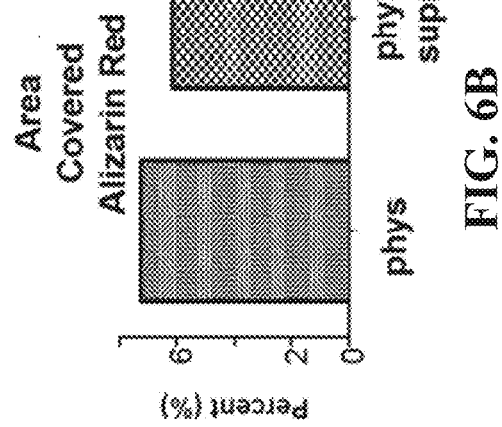
FIG. 6B is a chart showing a physiologic study of bone cells, whereby alizarin red stains were used to compare physiologic/supraphysiologic loadings of bone cells in accordance with the various concepts and disclosures presented herein.

Preliminary quantification of bone formation as a function of osteocyte loading was completed using the remaining CM from the experiments summarized in FIG. 5. Studies were completed on confluent osteoblasts induced to differentiate; alizarin red and von Kossa stains are presented in FIG. 6A. In comparison to physiologically/supraphysiologically stimulated osteocytes, CM from physiologically stimulated osteocytes resulted in an increase in bone formation of 18% as indicated by alizarin red stain (FIG. 6B), 21% as indicated by von Kossa stain (FIG. 6C) and 36% as indicated by alizarin red extraction (FIG. 6d) (mean 25%). Given a small sample size (n=3 or 6), rigorous statistics were not completed. Consistent with independent classification of loading effects on osteocyte activity, however, physiologic loads that increased osteocyte activity had the expected effects of increasing osteoblast activity and bone formation. Similarly, physiologic/supraphysiologic loads that decreased osteocyte activity and incorporated overload as determined by LDH staining had the effects of decreasing osteoblast activity and bone formation.

2.3 Design and Fabrication of Functional Activity LOC

Figures 7A, 7B, 7C, 7D, 7E, 7F:
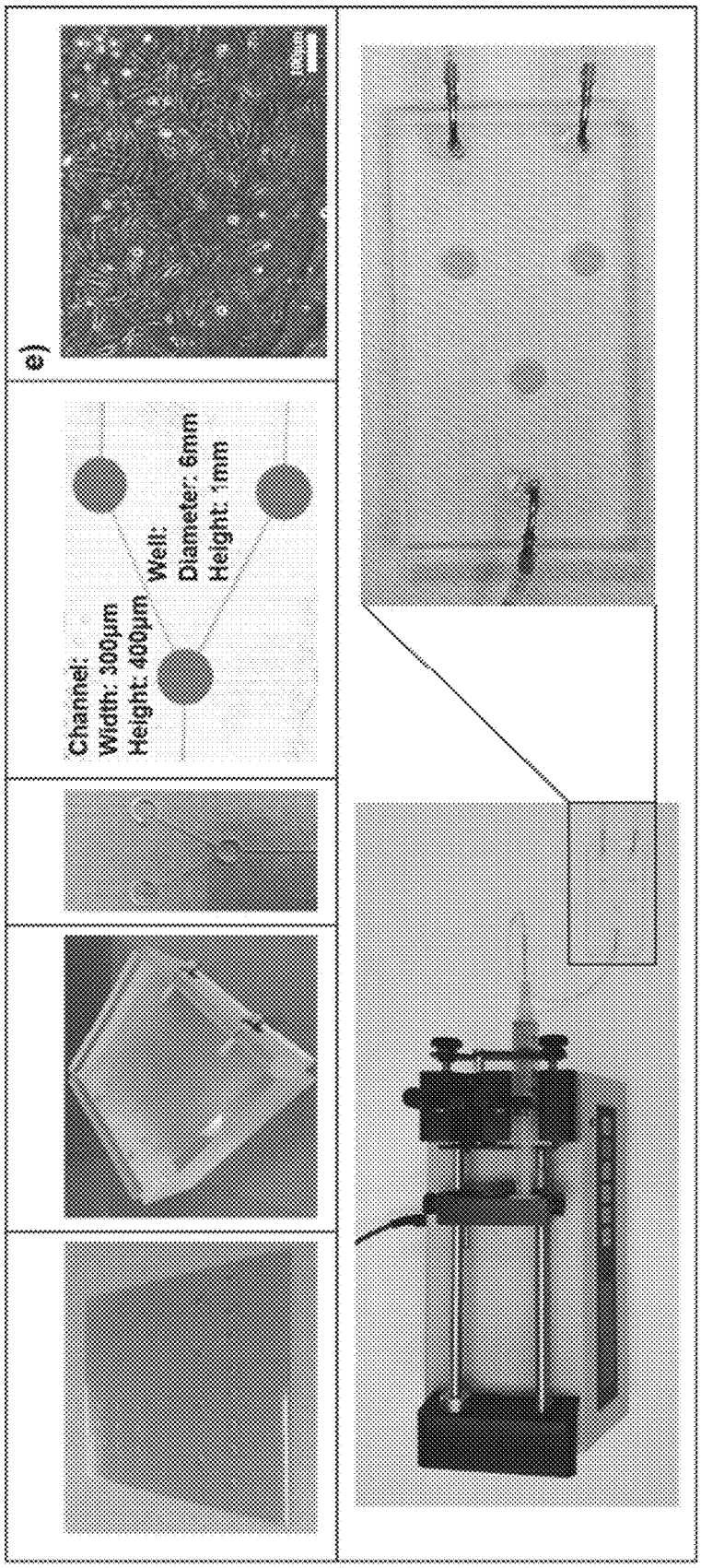
FIG. 7A is a diagrammatic view of a Prototherm 12120 mask used to form the LOC in accordance with the various concepts and disclosures presented herein.
FIG. 7B is a diagrammatic view of a Plexiglass™ box in which PDMS was poured onto the mask placed therein; the box enables well thicknesses to be adjusted and contains leveling screws in a tripod configuration to maintain alignment in accordance with the various concepts and disclosures presented herein.
FIG. 7C is a diagrammatic view of the lab-on-a-chip (LOC) formed from the mask of FIG. 7A, whereby the finished LOC houses channels 300 μm wide and 400 μm in height and wells 6 mm in diameter and 1 mm in height in accordance with the various concepts and disclosures presented herein.
FIG. 7D is a diagrammatic view of the lab-on-chip (LOC) shown in FIG. 7C, in accordance with the various concepts and disclosures presented herein.
FIG. 7E is a diagrammatic view of MLO-Y4 osteocytes that were imaged within the LOC of FIG. 7C after 72 hours in culture in accordance with the various concepts and disclosures presented herein.
FIG. 7F is a diagrammatic view in which a syringe of a picopump administers cell culture medium to microchannels and wells of the LOC shown in FIG. 7C in accordance with the various concepts and disclosures presented herein.

The mask, Plexiglass box and PDMS platform used in fabrication of the functional activity LOC are illustrated in FIGS. 7A-F. The mask contained three different well configurations (FIG. 7A). The box (FIG. 7B) was equipped with leveling screws in a tripod configuration to ensure the mask remained level at all times and that a uniform well thickness of 0.5 mm was reproducible. The PDMS platform is shown with channel 30 connected wells 20 prior to the addition of bone cells. The wells 20 were 6 mm in diameter to accommodate commercial substrates. Channel widths and heights are 300 µm and 400 µm, respectively (FIG. 7C-D). FIG. 7E depicts MLO-Y4 osteocytes cultured in the LOC at 72 hours, whereas in FIG. 7F, an LOC containing cell culture medium is shown to demonstrate adequate filling. Evaporation studies (not shown) revealed that daily evaporation did not exceed 3%. Therefore, evaporation was not a concern given feedings will occur every 3 days.

2.4. Verification of Osteoblast Bone Formation in Functional Activity LOC

MC3T3-E1 cells induced to differentiate formed bone on TC treated plates and polystyrene discs as well as on polystyrene discs within LOCs. Except with regard to the 16-day time point, concentrations of alizarin red extracted from TC treated plates at each time point (days 1, 2, 4 and 8 post-induction) were significant compared to the concentration at day 26 (2826 µM). Rhodamine phalloidin and DAPI staining (FIG. 8A) show confluent monolayers, as well as typical osteoblast proliferation and morphology on plates at days 1, 2 and 16. SEM imaging (FIG. 8B) further confirms expected morphology and monolayer formation. Mineralization in LOCs (FIG. 8C) at day 49 is indicated by alizarin red, which stains calcium (top), and von Kossa, which stains phosphate (bottom). A direct comparison of surface area covered (FIG. 8D) revealed there was no significant difference in areas covered by calcium and phosphate (p-value: 0.1186). Percentages averaged 10.72% and 6.43%, respectively. EDX (FIG. 8E) revealed that nodule formation on TC treated polystyrene discs contained the expected Ca/P ratio of 1.7, indicating a strong correlation to native bone content. No bone formation was observed in any of the non-induced cultures.

2.5. Verification of Osteoclast Bone Resorption in Functional Activity LOC

As shown in FIG. 9A, RAW 264.7 cells undergo osteoclastogenesis by 4 days post-induction. TRAP activity was decreased by 46% between days 4 and 5 and by 63% between days 4 and 10. Therefore, it was determined that TRAP production was optimal at day 4 (FIG. 9C). SEM verified formation of resorption pits on bone wafers by 20 days in TC treated plates (FIG. 9B). Quantification of bone resorption via pit staining with toluidine blue was completed following 20 days of culture within plates and following 30 days of culture within LOCs (FIG. 9D). The percentages of area resorbed by osteoclasts seeded within LOCs at 1,500 cells/well and at 56,000 cells/well after 30 days were not significantly different from the percentage of area resorbed by osteoclasts seeded at 1,000 cells/well after 20 days.

Therefore, one advantage of the various embodiments disclosed herein is that a lab-on-a-chip (LOC) may be utilized for the research of one or more bone cell types, including: osteocytes, osteoblasts, and osteoclasts, while removing in vivo temporal and spatial limitations. Another advantage of the various embodiments disclosed herein is that the LOC recapitulates the in vivo function of bone to enable the investigation in bone physiology, including conditions and diseases that is not possible with single cell in vitro or in vivo models, including but not limited to: fracture healing, distraction osteogenesis, osteoporosis, osteopetrosis, osteonecrosis (such as in response to bisphosphonates) bone metastasis, osteolysis, osteonecrosis, bone tissue engineering, and implant osteolysis. Still another advantage of the various embodiments disclosed herein is that the LOC may be used to investigate the effects of mechanical trauma or forces that are applied to bone tissue or cells activity, the effects of debris or particulates disposed in connection with bone tissue or cell activity, the effects of micro gravity or zero gravity on bone tissue or cells activity, and the effects of investigational new drugs (IND) on bone tissue or cell activity for quantifying unintended side effects of such drugs.

Therefore, it can be seen that the objects of the various embodiments disclosed herein have been satisfied by the structure and its method for use presented above. While in accordance with the Patent Statutes, only the best mode and preferred embodiments have been presented and described in detail, with it being understood that the embodiments disclosed herein are not limited thereto or thereby. Accordingly, for an appreciation of the true scope and breadth of the embodiments, reference should be made to the following claims.

What is claimed is:

1. A method of analyzing bone cells using a lab-on-a-chip (LOC) comprising:
   configuring a LOC having a substrate with an arrangement of a plurality of coupled wells connected by at least one tube extending from each said well;
   attaching a cap to said substrate to seal said plurality of fluidly coupled wells and said at least one tube, wherein access to said at least one tube is through a port extending through said cap;
   providing at least one bone cell type in a first one of said plurality of wells, and at least one bone cell type in a second one of said plurality of wells, wherein said at least one bone cell type in said second one of said plurality of wells is combined with a second cell type, to form a co-culture;
   applying a treatment condition through said port to said at least one bone cell type in said first well to generate a conditioned medium (CM) therefrom;
   flowing said CM to said second well having at least one bone cell type with said co-culture through said at least one tube; and
   quantifying an amount of bone formation or bone absorption that occurs in said at least one bone cell type with said co-culture in said second well in response to said CM.

2. The method of claim 1, further comprising:
   selectively coating said substrate and said cap, which are formed of polydimethylsiloxane (PDMS), with at least collagen and osteocytes.

3. The method of claim 2, further comprising:
   selectively coating one of said second one of said plurality of wells with collagen, bone wafer and osteoclasts; or collagen coated plastic discs and osteoblasts.

4. The method of claim 1, wherein said at least one bone cell type at said first well includes at least osteocytes.

5. The method of claim 4, wherein said at least one bone cell type at said second well includes one or more of osteocytes, osteoclasts, and osteoblasts.

6. The method of claim 1, wherein said treatment condition includes one or more of: mechanical force loading, mechanical force unloading, a chemical, a chemical compound, an electrical signal, an electrical field, a magnetic field, particulate material, and zero-gravity.

7. The method of claim 1, further comprising:
   selectively activating or deactivating soluble signals generated from said cell types in at least one of said first well or said second well by inserting through said port at least one hone cell co-factor.

8. The method of claim 7, wherein said activating or deactivating step is performed by fluidly delivering at least one bone cell co-factor in at least one of said first well or said second well.

9. The method of claim 1, further comprising:
   quantifying a functional amount of bone formation that occurs in said second well for more than 72 hours up to 1176 hours.

10. The method of claim 1, further comprising:
    quantifying a functional amount of bone formation or bone resorption that occurs in said second well for more than 72 hours up to 480 hours.

11. The method of claim 1, further comprising:
    quantifying a functional amount of hone resorption that occurs in said second well for more than 72 hours up to 720 hours.

12. The method of claim 1, wherein:
    the step of quantifying comprises removing the cap and accessing the contents of said plurality of wells to determine the amount of bone formation or bone absorption that has occurred.

13. A method of analyzing bone cells using a lab-on-a-chip (LOC) comprising:
    configuring a LOC with an arrangement of a plurality of fluidly coupled wells;
    providing at least osteocytes in a first one of said plurality of wells, and at least one bone cell type in a second one of said plurality of wells, wherein either of said osteocytes in said first one of said plurality of wells or said at least one bone cell type in said second one of said plurality of wells is combined with one or more other cell type to form a co-culture;

applying a treatment condition to at least said osteocytes in said first well to generate a conditioned medium (CM) therefrom;

flowing said CM from said first well to said second well having said at least one bone cell type; and quantifying an amount of bone formation or bone absorption that occurs in said at least one bone cell type in said second well in response to said CM or said co-culture after more than 72 hours and up to 1176 hours.

14. The method of claim 13, further comprising:
providing osteoclasts, osteoblasts, or an osteoblast/osteoclast co-culture in said second well.

15. The method of claim 14, further comprising:
providing at least one bone cell type in said second well selected from the group consisting of osteocytes, osteoclasts, and osteoblasts.

16. The method of claim 13, further comprising:
quantifying a functional amount of bone formation that occurs in said second well for more than 72 hours up to 1176 hours.

17. The method of claim 13, further comprising:
quantifying a functional amount of bone resorption that occurs in said second well for more than 72 hours up to 720 hours.

18. The method of claim 13, wherein: the step of quantifying comprises opening said LOC and accessing the contents of said plurality of wells to determine the amount of bone formation or bone 4 absorption that has occurred.

* * * * *